United States Patent
Tobjork et al.

(10) Patent No.: US 12,228,556 B2
(45) Date of Patent: Feb. 18, 2025

(54) GAS SENSOR

(71) Applicant: Sumitomo Chemical Co., Ltd., Tokyo (JP)

(72) Inventors: Daniel Tobjork, Cambridgeshire (GB); Pascal Cachelin, Cambridgeshire (GB); Robert Archer, Cambridgeshire (GB)

(73) Assignee: Sumitomo Chemical Co., Ltd., Tokyo (JP)

( * ) Notice: Subject to any disclaimer, the term of this patent is extended or adjusted under 35 U.S.C. 154(b) by 225 days.

(21) Appl. No.: 17/911,514

(22) PCT Filed: Mar. 12, 2021

(86) PCT No.: PCT/EP2021/056322
§ 371 (c)(1),
(2) Date: Sep. 14, 2022

(87) PCT Pub. No.: WO2021/185690
PCT Pub. Date: Sep. 23, 2021

(65) Prior Publication Data
US 2023/0358714 A1    Nov. 9, 2023

(30) Foreign Application Priority Data

Mar. 16, 2020 (WO) .............. PCT/GB2020/050667

(51) Int. Cl.
*G01N 33/00*    (2006.01)

(52) U.S. Cl.
CPC ..... *G01N 33/0047* (2013.01); *G01N 33/0014* (2013.01); *G01N 33/0016* (2013.01); *G01N 33/0031* (2013.01)

(58) Field of Classification Search
CPC .............. G01N 33/0031; G01N 33/0016
See application file for complete search history.

(56) References Cited

U.S. PATENT DOCUMENTS

| | | | |
|---|---|---|---|
| 4,960,658 A | | 10/1990 | Ikeno et al. |
| 5,531,218 A | * | 7/1996 | Krebs .................. G01N 33/497 |
| | | | 128/202.22 |

(Continued)

FOREIGN PATENT DOCUMENTS

| | | | |
|---|---|---|---|
| CN | 106555712 A | * | 4/2017 |
| DE | 10159616 A1 | | 6/2003 |

(Continued)

OTHER PUBLICATIONS

International Search Report and Written Opinion mailed Aug. 3, 2020, in connection with International Application No. PCT/GB2020/050667.

(Continued)

*Primary Examiner* — Jamel E Williams
(74) *Attorney, Agent, or Firm* — Wolf, Greenfield & Sacks, P.C.

(57) ABSTRACT

A gas sensor apparatus (100) comprising a gas inlet (10); a first gas sensor (40); a first gas flow path between the inlet and the gas sensor; a humidifier (20) disposed between the gas inlet and the gas sensor in the first gas flow path of the gas sensor apparatus; and a dehumidifier (30) disposed between the humidifier and the first gas sensor in the first gas flow path. The gas sensor apparatus may have more than one gas flow path. The gas sensor apparatus may contain more than one sensor. The gas sensor apparatus may contain one or more filters for filtering a target gas or a non-target gas. The gas sensor apparatus may be used in detection of ethylene and/or 1-methylcyclopropene.

15 Claims, 6 Drawing Sheets

(56) References Cited

U.S. PATENT DOCUMENTS

| | | | | |
|---|---|---|---|---|
| 5,542,284 | A | * | 8/1996 | Layzell .............. G01N 33/0024 73/23.21 |
| 6,132,492 | A | * | 10/2000 | Hultquist ............. B01D 53/229 95/902 |
| 6,220,076 | B1 | * | 4/2001 | Layzell .............. G01N 33/0031 73/23.21 |
| 2001/0027678 | A1 | | 10/2001 | Mottram et al. |
| 2008/0053439 | A1 | * | 3/2008 | Lighton ............... G01N 33/497 128/204.22 |
| 2009/0302230 | A1 | | 12/2009 | Birks et al. |
| 2011/0156715 | A1 | | 6/2011 | Groves |
| 2016/0199605 | A1 | * | 7/2016 | Hamilton .......... A61M 16/0069 128/205.12 |
| 2016/0213879 | A1 | * | 7/2016 | Parthasarathy ..... A61M 16/208 |
| 2016/0355934 | A1 | * | 12/2016 | Yoshinaga ................ C25B 9/19 |
| 2019/0173114 | A1 | * | 6/2019 | Sakai ............... H01M 8/04164 |
| 2019/0252168 | A1 | * | 8/2019 | Chhabra ............ H01J 49/0431 |
| 2020/0041443 | A1 | * | 2/2020 | Newsome .......... G01N 27/4141 |
| 2020/0147883 | A1 | * | 5/2020 | Kennedy ................ B33Y 50/02 |
| 2021/0027678 | A1 | | 1/2021 | Long |
| 2021/0341444 | A1 | * | 11/2021 | Fan .................... G01N 33/0016 |
| 2021/0381116 | A1 | * | 12/2021 | Kashi ........................ C25B 9/77 |
| 2022/0187265 | A1 | | 6/2022 | Tobjork et al. |

FOREIGN PATENT DOCUMENTS

| | | | | |
|---|---|---|---|---|
| DE | 102010014222 | B4 | * | 3/2019 ......... G01N 33/0031 |
| GB | 2561246 | A | | 10/2018 |
| JP | S58166254 | | | 10/1983 |
| WO | WO 2004/027410 | A1 | | 4/2004 |
| WO | WO 2007/030206 | A2 | | 3/2007 |
| WO | WO 2015/170980 | A1 | | 11/2015 |
| WO | WO-2019187530 | A1 | * | 10/2019 ............... G01F 1/36 |

OTHER PUBLICATIONS

International Search Report and Written Opinion mailed Jun. 11, 2021, in connection with Application No. PCT/EP20210/056322.
Combined Search and Examination Report dated Aug. 15, 2019, in connection with GB Application No. 1903473.5.
Zhang et al., Mechanism of NO2 detection in carbon nanotube field effect transistor chemical sensors. Applied Physics Letter 88. Mar. 23, 2006. 3 pages.

* cited by examiner

GAS SENSOR

RELATED APPLICATIONS

This application is a National Stage filing under 35 U.S.C. § 371 of International Patent Application Serial No. PCT/EP2021/056322, filed Mar. 12, 2021, which claims priority to International Patent Application Serial No. PCT/GB2020/050667, filed Mar. 16, 2020. The entire contents of these applications are incorporated herein by reference in their entirety.

BACKGROUND

Embodiments of the present disclosure relate to apparatus and methods for sensing a target gas in an environment.

SUMMARY

In some embodiments, the present disclosure provides a gas sensor apparatus comprising a gas inlet; a first gas sensor; a first gas flow path between the inlet and the gas sensor; a humidifier disposed between the gas inlet and the gas sensor in the first gas flow path of the gas sensor apparatus; and a dehumidifier disposed between the humidifier and the first gas sensor in the first gas flow path.

Optionally, the dehumidifier is a solid dehumidifier. Optionally, the dehumidifier is a solid salt dehumidifier.

Optionally, the humidifier is a salt solution or gel.

Optionally, the apparatus comprises a second gas flow path between the inlet and the gas sensor. Optionally, the second gas flow path comprises a target gas filter disposed between the inlet and the first gas sensor wherein the target gas filter is configured to filter a target gas from an input gas.

Optionally, the gas sensor apparatus further comprises a non-target gas filter configured to filter a non-target gas from an input gas.

Optionally, the first gas flow path does not comprise a filter disposed between the inlet and the gas sensor.

Optionally, the first gas sensor is a resistive sensor or a capacitive sensor.

Optionally, the gas sensor apparatus further comprises a second gas sensor. In some embodiments, the first and second gas sensors are the same. In some embodiments, the first and second gas sensors are different.

In some embodiments, the present disclosure provides a method of detecting the presence or concentration of a target gas in a sample gas, the method comprising:
  forming a humidifier-treated gas comprising exposing the sample gas to a humidifier;
  forming a dehumidifier-treated gas comprising exposing the humidifier-treated environmental gas to a dehumidifier; and
  measuring a response of a gas sensor to the dehumidifier-treated gas.

Optionally, the target gas is an organic compound.

Optionally, the target gas is an alkene.

Optionally, the target gas is ethylene or 1-methylcyclopropene.

DESCRIPTION OF THE DRAWINGS

The disclosed technology and accompanying figures describe some implementations of the disclosed technology.

Figure 1:
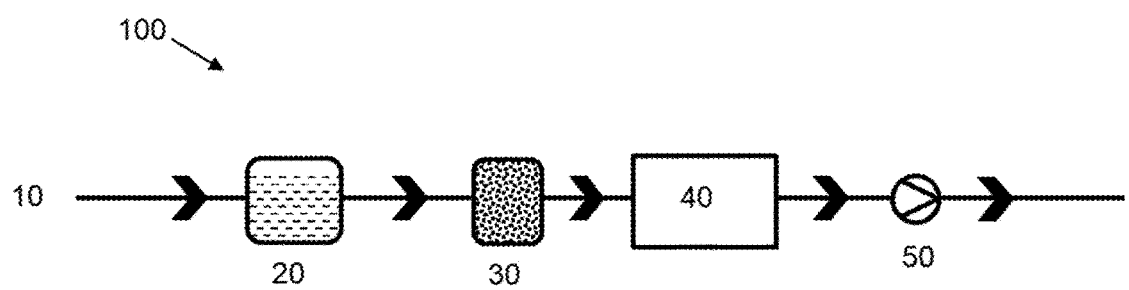
FIG. 1 schematically illustrates gas sensor apparatus according to some embodiments in which the apparatus has a single gas flow path.

The drawings are not drawn to scale and have various viewpoints and perspectives. The drawings are some implementations and examples. Additionally, some components and/or operations may be separated into different blocks or combined into a single block for the purposes of discussion of some of the embodiments of the disclosed technology. Moreover, while the technology is amenable to various modifications and alternative forms, specific embodiments have been shown by way of example in the drawings and are described in detail below. The intention, however, is not to limit the technology to the particular implementations described. On the contrary, the technology is intended to cover all modifications, equivalents, and alternatives falling within the scope of the technology as defined by the appended claims.

DETAILED DESCRIPTION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, electromagnetic, or a combination thereof. Additionally, the words "herein," "above," "below," and words of similar import, when used in this application, refer to this application as a whole and not to any particular portions of this application. Where the context permits, words in the Detailed Description using the singular or plural number may also include the plural or singular number respectively. The word "or," in reference to a list of two or more items, covers all of the following interpretations of the word: any of the items in the list, all of the items in the list, and any combination of the items in the list.

The teachings of the technology provided herein can be applied to other systems, not necessarily the system described below. The elements and acts of the various examples described below can be combined to provide further implementations of the technology. Some alternative implementations of the technology may include not only additional elements to those implementations noted below, but also may include fewer elements.

These and other changes can be made to the technology in light of the following detailed description. While the description describes certain examples of the technology, and describes the best mode contemplated, no matter how detailed the description appears, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while some aspect of the technology may be recited as a computer-readable medium claim, other aspects may likewise be embodied as a computer-readable medium claim, or in other forms, such as being embodied in a means-plus-function claim.

In the following description, for the purposes of explanation, numerous specific details are set forth in order to provide a thorough understanding of implementations of the disclosed technology. It will be apparent, however, to one skilled in the art that embodiments of the disclosed technology may be practiced without some of these specific details.

Methods introduced here can be embodied as special-purpose hardware (e.g., circuitry), as programmable circuitry appropriately programmed with software and/or firmware, or as a combination of special-purpose and programmable circuitry. Hence, embodiments may include a machine-readable medium having stored thereon instructions which may be used to program a computer (or other electronic devices) to perform a process. The machine-readable medium may include, but is not limited to, floppy diskettes, optical disks, compact disc read-only memories (CD-ROMs), magneto-optical disks, ROMs, random access memories (RAMs), erasable programmable read-only memories (EPROMs), electrically erasable programmable read-only memories (EEPROMs), magnetic or optical cards, flash memory, or other type of media/machine-readable medium suitable for storing electronic instructions. The machine-readable medium includes non-transitory medium, where non-transitory excludes propagation signals. For example, a processor can be connected to a non-transitory computer-readable medium that stores instructions for executing instructions by the processor.

Gas sensors may be used in settings which are subject to changes in humidity, e.g. due to changes in atmospheric temperature and/or pressure. These changes may affect the accuracy of the gas sensor, for example because the gas sensor is sensitive to moisture or because optimal operation of the gas sensor is within a specific humidity window. Accordingly, humidity may affect the magnitude and/or kinetics of a gas sensor's response to a gas.

The present inventors have found that fluctuations in humidity of a gas reaching a gas sensor can be reduced by exposing the gas to a humidifier followed by a dehumidifier before the gas reaches the gas sensor.

FIG. 1 illustrates gas sensor apparatus 100 according to an embodiment of the present disclosure. The apparatus provides a gas flow path between an inlet 10 and an outlet 80 of the apparatus in which the gas comes into contact with, in sequence, a humidifier 20 and a dehumidifier 30 before the gas reaches gas sensor 40. The humidity of a gas reaching the gas sensor following humidification and dehumidification is preferably stable within a window of ±10%. The humidity of the gas reaching the gas sensor 40 is optionally in the range of about 15-90%.

The apparatus may comprise one or more other components for altering the composition of the gas before it reaches the gas sensor, for example one or more filters for removing one or more substances other than a target gas. The apparatus may comprise more than one dehumidifier between the inlet and the gas sensor, for example a second dehumidifier between the humidifier 20 and the gas sensor.

The gas sensor apparatus may comprise a pump 50 disposed downstream of the inlet, and preferably between the gas sensor and the outlet 80, so as to draw gas through the apparatus.

A presence, concentration or a change in concentration of the target material may be determined from a measurement of the gas sensor or a derivative thereof.

In some embodiments, the gas sensor apparatus may have a single gas flow path between an inlet and an outlet, for example as illustrated in FIG. 1.

In some embodiments, the gas sensor apparatus may comprise two or more gas flow paths between the inlet and outlet.

The gas sensor apparatus may include a filter for filtering at least one of a target gas; a contaminant gas, e.g. a contaminant gas which the gas sensor is sensitive to, for example an organic compound (other than the target gas if the target gas is an organic compound); and particulates.

The gas sensor apparatus may comprise two or more gas flow paths having a common region in which a contaminant gas filter and/or particulate filter is disposed. A filter in a common region of the apparatus may be used in combination with a dehumidifier upstream of the filter; a reduction in humidity of input gas before reaching the filter may increase the operational lifetime of the filter. It will be understood that a dehumidifier is not a filter as described herein.

In some preferred embodiments, the two or more gas flow paths include a first gas flow path which does not include a filter and a second gas flow path which does include a filter.

In some preferred embodiments, the apparatus has two or more gas flow paths and a filter is disposed in at least two of the gas flow paths. In some embodiments, the same filter is common to two or more flow paths. In some embodiments, at least two flow paths each contain at least one filter which is unique to that gas flow path. In some embodiments, a filter for a target gas is disposed in one of the plurality of gas flow paths and a filter for a contaminant gas is disposed in another gas flow path or in a region common to the two at least two flow paths. It will be understood that the two or more flow paths include at least one flow path in which the gas comes into contact with, in sequence, a humidifier and a dehumidifier before the gas reaches gas sensor. Preferably, gas in each gas flow path comes into contact with, in sequence, a humidifier and a dehumidifier.

Flow of gas in the two or more gas flow paths may be controlled by one or more valves. The one or more valves may be, without limitation, two-way or three-way valves. The one or more valves of the gas sensor as described herein are referred to herein as "a valve arrangement".

Figure 2:
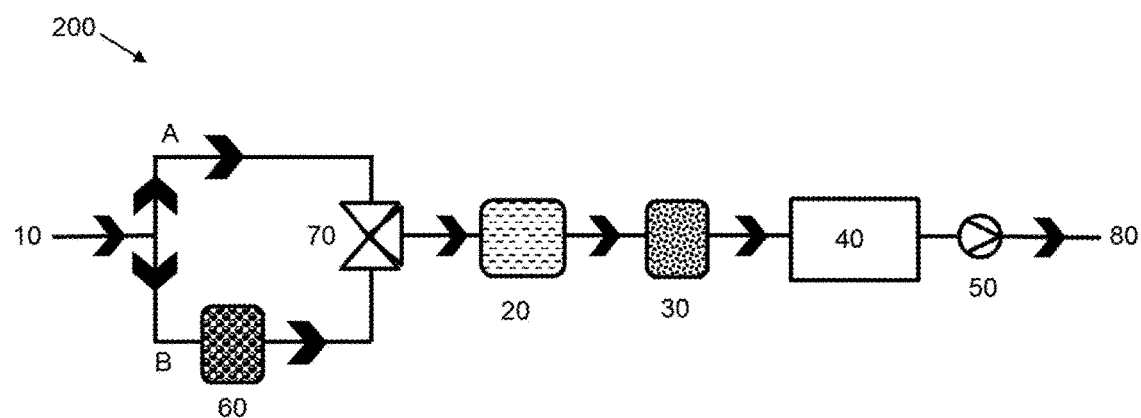
FIG. 2 schematically illustrates gas sensor apparatus according to some embodiments in which the apparatus has a first gas flow path in which gas drawn from the environment is not filtered and a second gas flow path in which gas drawn from the environment is filtered and a gas sensor which may be cycled between exposure to gases from the first and second gas flow paths.

FIG. 2 illustrates gas sensor apparatus 200 according to an embodiment in which the apparatus has two gas flow paths in which a first gas flow path A between the inlet and the outlet does not contain any filters and a second gas flow path B between the inlet 10 and the outlet 80 includes a filter 60 for removal of any target gas in the gas drawn into the inlet. The gas flow paths are controlled by valve arrangement 70; in FIG. 2, the valve arrangement is a single three-way valve is used however it will be appreciated that other valve arrangements may be used, for example two two-way valves.

In the case where the gas sensor apparatus comprises two or more gas flow paths, the humidifier and dehumidifier are preferably disposed in a region of the gas sensor apparatus which is common to all of the gas flow paths.

The gas sensor may be exposed to alternating flows of gas from gas flow paths A in which the gas sensor apparatus is in a first state and gas from gas flow paths B in which the gas sensor apparatus is in a second state.

The presence, concentration or a change in concentration of the target material may be determined by subtracting a gas sensor measurement or a derivative thereof in the second state from the gas sensor measurement or a derivative thereof in the first state. This determination may be made without needing a separate background reading.

Figure 3:
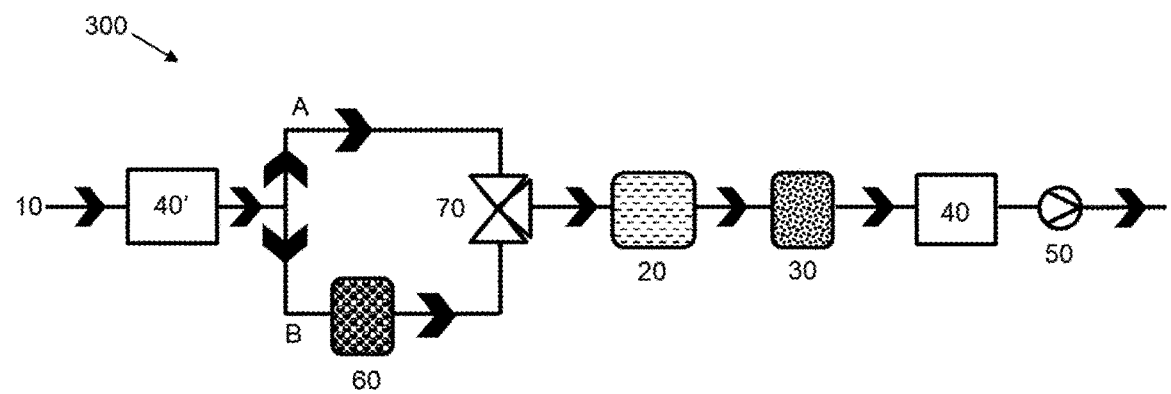
FIG. 3 schematically illustrates gas sensor apparatus as described for FIG. 2 and further comprising a second gas sensor which is continuously exposed to unfiltered gas.

In some embodiments, the gas sensor 40 is the only gas sensor of the gas sensor apparatus. In some embodiments, the gas sensor apparatus contains two or more gas sensors. The two or more gas sensors may be the same or different. FIG. 3 illustrates gas sensor apparatus 300 as illustrated in FIG. 2 and further containing a second gas sensor 40' disposed upstream of the valve arrangement 70 for selection of the first or second gas flow path; as such, the second gas sensor is disposed in a region common to both the first and second gas flow paths. In operation, the second gas sensor is exposed only to gas from which any target material has not been filtered. The first gas sensor is exposed to filtered or unfiltered gas, as described with reference to FIG. 2, depending on which state the gas sensor is in. The gas sensor apparatus may be cycled between a first and second states state in which the first gas sensor is exposed to unfiltered and filtered gas, respectively.

FIG. 3 illustrates gas sensor apparatus in which gas reaching second gas sensor 40' has not been subjected to humidification or dehumidification. In other embodiments, gas is humidified and/or dehumidified before reaching the second gas sensor 40'. Humidification only, dehumidification only or both of humidification and dehumidification may be selected according to the optimal humidity for operation of the second gas sensor 40'. Dehumidification of input air may extend the lifetime of the gas sensor apparatus or components thereof.

In some embodiments, the gas sensor apparatus contains a first gas sensor for detection of a first target gas and a second gas sensor for detection of a second target gas.

In some embodiments, the gas sensor apparatus contains two gas sensors for detection of the same gas at different concentrations. A first gas sensor may be configured to detect a target gas at low concentrations, e.g. below 100 ppm or below 10 ppm, and a second gas sensor may be configured to detect the same target gas at high concentrations, e.g. greater than or equal to 100 ppm or 10 ppm, respectively.

The periodic measurements of the first gas sensor of target material concentrations allow for correction and/or calibration of the continuous measurement of the second gas sensor. Thus, the effect of drift in the sensor measurements may be controlled for.

Figure 4:
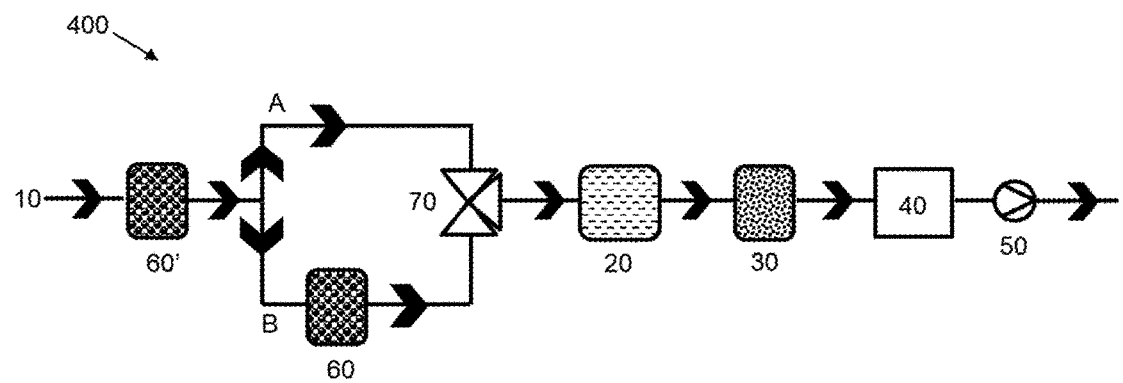
FIG. 4 schematically illustrates gas sensor apparatus as described for FIG. 2 and further comprising a filter in a region common to the first and second gas flow paths.

FIG. 4 illustrates gas sensor apparatus illustrates gas sensor apparatus 400 as described with reference to FIG. 2 and further containing a second filter 60' disposed upstream of the valve arrangement 70 for selection of the first or second gas flow path; as such, the second filter 60' is disposed in a region common to both the first and second gas flow paths. Gas filter 60' may filter at least one of a contaminant gas, e.g. a contaminant gas which the gas sensor is sensitive to, for example an organic compound (other than the target gas if the target gas is an organic compound); and particulates.

Figure 5:
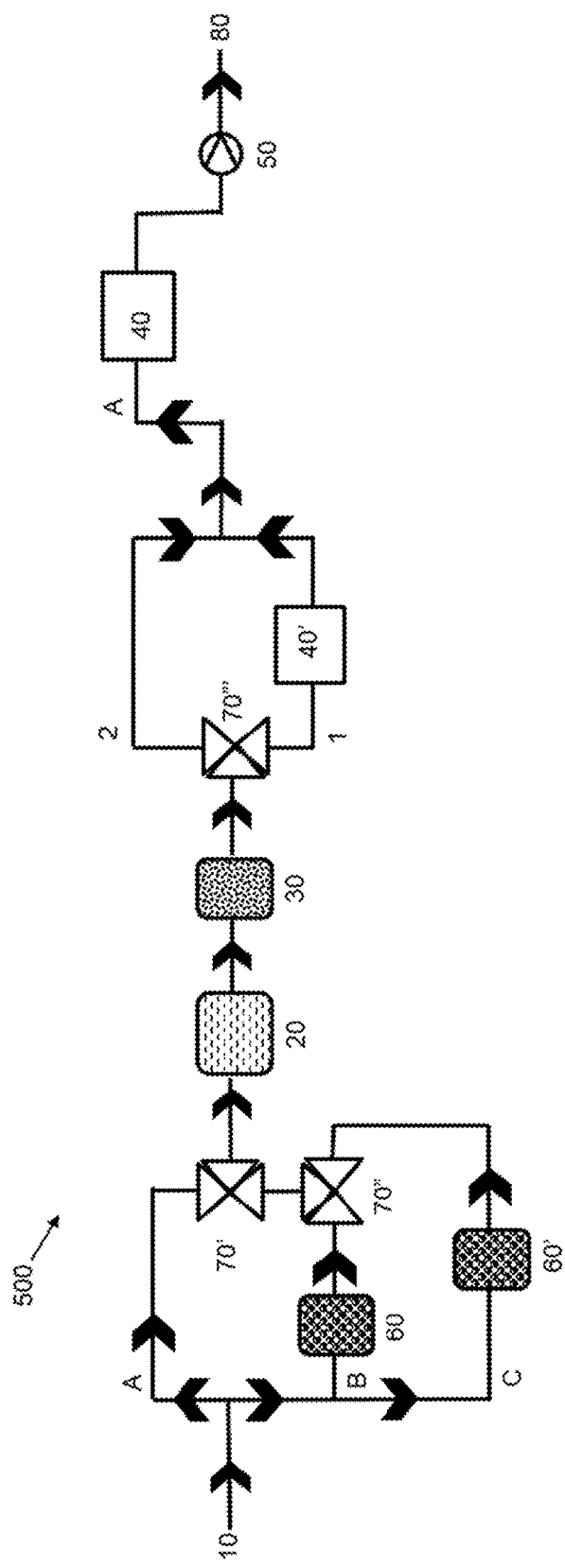
FIG. 5 schematically illustrates gas sensor apparatus according to some embodiments in which the apparatus has two different filters and two different gas sensors.

FIG. 5 illustrates gas sensor apparatus containing two different filters 60 and 60' and two sensors 40 and 40'. The gas sensor apparatus has a gas flow path A having no filters; a gas flow path B including filter 60; and a gas flow path C having filter 60'. The selection of gas flow paths A, B and C is controlled by valves 70' and 70".

Each of these flow paths includes a sub-flow path selected from sub-flow path 1 in which the gas is brought into contact with sensor 40' and then sensor 40, and sub-flow path 2 in which the gas is brought into contact with sensor 40 only. Entry into sub-flow paths 1 and 2 is controlled by valve 70'".

The sensors 40 and 40' may be different sensors for configured for detection of different gases. The filters 60 and 60', and the choice of whether the gas is brought into contact with only one sensor or with both sensors, may be selected according to the sensitivities of the gas sensors 40 and 40' to gases in the input atmosphere.

In some embodiments, the gas sensor apparatus is for detection of ethylene target gas and 1-methylcyclopropene (1-MCP) target gas. The filter 60 in gas flow path B may remove 1-MCP. The filter 60' may remove volatile organic compounds and ethylene. Exemplary materials for removal of ethylene include, without limitation, activated carbon; palladium supported on activated carbon; palladium supported on activated alumina; a permanganate, supported on activated alumina; permanganate-impregnated activated carbon; molecular sieves; and aluminosilicates. A permanganate as described herein may be, for example, sodium or potassium permanganate. Mixtures of materials described herein may be used, e.g. for removal of two or more compounds such as ethylene and one or more volatile organic compounds.

The sensor 40 may be configured to detect i-MCP. The sensor 40' may be configured to detect ethylene. Removal of 1-MCP and removal of volatile organic compounds and ethylene allow for sensors 40 and 40' respectively to be recalibrated to a baseline and may avoid poisoning due to long-term exposure to the gas the sensor is responsive to.

In use, sensor 40' is optionally not exposed to gases from one or two of gas flow paths A, B and C whereas sensor 40 may be exposed to gases from each of gas flow paths A, B and C.

It will be understood that other arrangements of a gas sensor, a humidifier, a dehumidifier and one or more additional components, e.g. one or more additional humidifiers, one or more additional dehumidifiers, one or more filters (including target and non-target gas filters) and/or at least one additional gas sensor may be provided such that a gas drawn from an environment may be delivered to a sensor following humidification and subsequent dehumidification of the gas.

Gas may flow through apparatus as described herein at a rate in the range of 5 $cm^3$/minute-1 L/minute, optionally 10-100 $cm^3$/minute.

Gas Sensor

The gas sensor may be a gas sensor having an optimal operating humidity window.

The gas sensor may be selected from, without limitation a capacitive, resistive, electrochemical or photoresponsive sensor. Exemplary sensors include, without limitation, a metal oxide sensor, a photoionization detector (PID) a non-dispersive infrared detector (NDIR), an electrochemical sensor and a field effect transistor sensor, for example a bottom-gate or top-gate thin film transistor. The thin film transistor may be an organic thin film transistor.

The one or more gas sensors of the gas sensor apparatus may be provided in removable cartridges.

Humidifier

The humidifier comprises or consists of water. Preferably, the humidifier comprises a salt solution, more preferably a saturated salt solution. The humidifier saturated salt solution may be in the form of a gel, e.g. a xanthan gum gel. It will be understood that any gel or solution which increases the humidity of an input gas may be used as a humidifier The humidity of the gas may be set to a predetermined level or range as described in, for example, L. B. Rockland, Anal. Chem. 1960, 32, 10, 1375. "Saturated Salt Solutions for Static Control of Relative Humidity between 5° and 40° C." or L. Greenspan, Journal of Research of the National Bureau of Standards-A. Physics and Chemistry Vol. 81 A, No. 1, 1977. "Humidity Fixed Points of Binary Saturated Aqueous Solutions", the contents of which are incorporated herein by reference.

Dehumidifier

The dehumidifier may be in solid, liquid or gel form.

Preferably, the dehumidifier is a solid, more preferably a solid salt. The present inventors have found that a solid salt dehumidifier may absorb little or none of a target organic compound, e.g. an alkene such as ethylene or 1-methylcyclopropene.

The solid dehumidifier may be selected from hygroscopic salts including, without limitation, an ammonium, alkali, alkali earth or transition metal salt. The salt may be, without limitation, a halide, hydroxide, sulfate, acetate, dichromate, formate or nitrate. Exemplary salts include, without limitation, $NH_4NO_3$, $(NH_4)_2SO_4$, LiCl, NaCl, $CaCl_2$, $MgCl_2$, KCl, KOH, KBr, KI, NaBr, $Mg(NO_3)_2$, $NaNO_3$, $KNO_3$, sodium or potassium acetate, sodium or potassium dichromate, calcium formate, copper sulfate or combinations thereof. The solid dehumidifier may have any form, e.g. powder, pellet, or flake form. A solid dehumidifier in a non-powder form is preferable to prevent spillage of the dehumidifier from the vessel containing it, e.g. during turning or tipping of the gas sensor apparatus, and to avoid blockage if gas flows though (rather than over a surface of) the vessel.

The solid dehumidifier may be selected according to a desired humidity, e.g. a humidity within an optimal humidity window of the gas sensor. A mixture of dehumidifiers may be used.

The present inventors have found that a solid dehumidifier may provide more stable dehumidification over time as compared to a non-solid dehumidifier.

The dehumidifier may comprise or consist of a saturated salt solution, e.g. a solution of a hygroscopic salt as described above.

The dehumidifier may comprise or consist of an ionic liquid.

It will be understood that any gel or solution which reduces the humidity of an input gas may be used as a dehumidifier.

The humidifier and dehumidifier as described herein may each independently be contained in any suitable vessel which, in use, allows gas flowing through the gas sensor apparatus to come into contact with the humidifier and, dehumidifier contained within their respective vessels. In some embodiments, the humidifier and/or dehumidifier vessel has an open or water-permeable top, e.g. a perforated top; in use, gas flowing over the vessel comes into contact with the humidifier or dehumidifier, respectively. In some embodiments, the dehumidifier is a solid contained in a gas-permeable vessel, e.g. a perforated vessel, such that gas flows through the vessel. The humidifier and/or dehumidifier vessel may be a removable cartridge, allowing the cartridge to be refilled or replaced as required.

The extent of humidification and dehumidification may be controlled by selection of parameters including one or more of: gas flow rate; humidifier; dehumidifier; humidifier and/or dehumidifier solid content in the case of a saturated solution humidifier or dehumidifier; humidifier surface contact area; and dehumidifier surface contact area.

Filter

The filter material may adsorb or absorb a target material to be sensed by the gas sensor and/or one or more non-target materials. The filter material may react with the target material and/or non-target material or materials.

In some embodiments, the filter material selectively removes only the target material from the gas it is exposed to. In some embodiments, the filter material is activated carbon. It will be understood that a target material filter may be used in apparatus having at least two flow paths wherein at least one of the flow paths does not contain a target material filter.

In other embodiments, a filter device, e.g. a mesh or HEPA filter for a particulate non-target material or a scrubber for a target or non-target compound, may be used.

Applications

The gas sensor apparatus as described herein may be used to monitor the presence or concentration of a target gas. The target gas is preferably an organic compound.

Ethylene produced by plants can accelerate ripening of climacteric fruit, the opening of flowers, and the shedding of plant leaves. 1-MCP is known for use in inhibiting such processes. Accordingly, the gas sensor apparatus and method as described herein may be used in monitoring the concentration of a gas in an environment, e.g. a concentration of ethylene and/or 1-MCP in a location where harvested fruit or plants are stored, such as a warehouse or store, or concentration of ethylene and/or 1-MCP during transportation of harvested fruit or plants.

EXAMPLES

A mass flow controller was used to control the flow of air through gas tubing to 50 $cm^3$/min. Humidity (and temperature) probes were placed in the flow stream at the input and output to the dehumidifier or both humidity control stages and connected via USB to a PC for logging the data via a LabView program. For generating input flow with high relative humidity (~90%) for the data in FIGS. 5, 6 and 9 the gas was first flowed over the surface of ~80 ml water inside a 100 ml glass vial.

Figure 6:
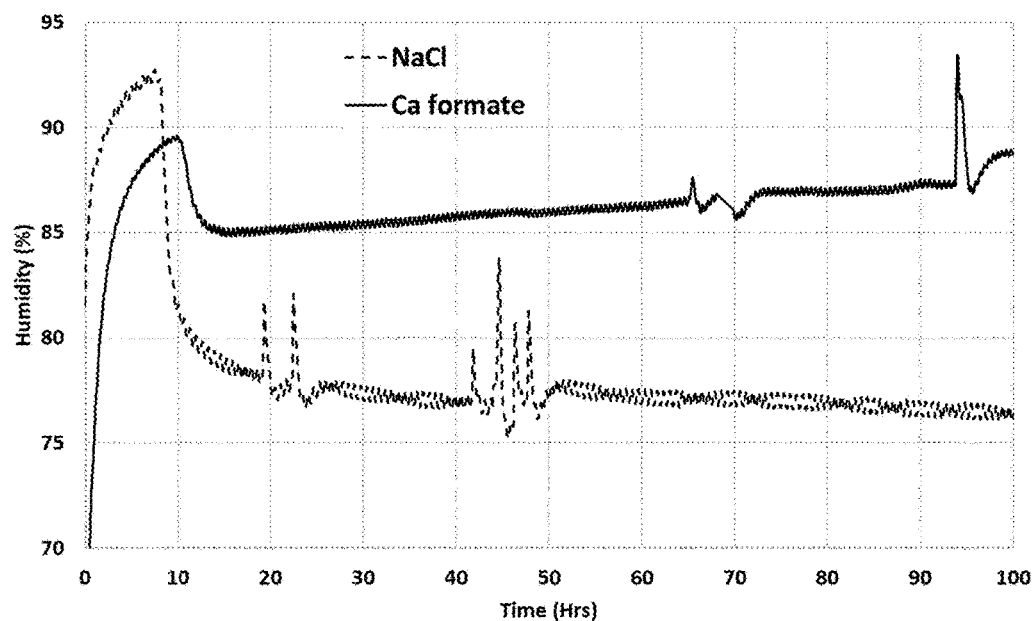
FIG. 6 is a graph of a change in humidity of dry air exposed to a NaCl humidifier and a calcium formate humidifier over time during which the temperature of the humidifier is initially reduced.

FIG. 6 is a plot of humidity vs. time for air produced by comparative apparatus in which dry air (relative humidity about 10%) has been passed over a gel humidifier of 5 wt % xanthan gum with a saturated solution of either NaCl or calcium formate in a refrigerator at about 5° C. in which the apparatus at room temperature is placed in a refrigerator at time 0. There is an initial sharp increase in humidity, which is attributed to cooling of the gel humidifiers without any associated condensation, thus illustrating that humidity of a gas treated in such a way may be variable if environmental parameters such as temperature vary.

Figure 7:
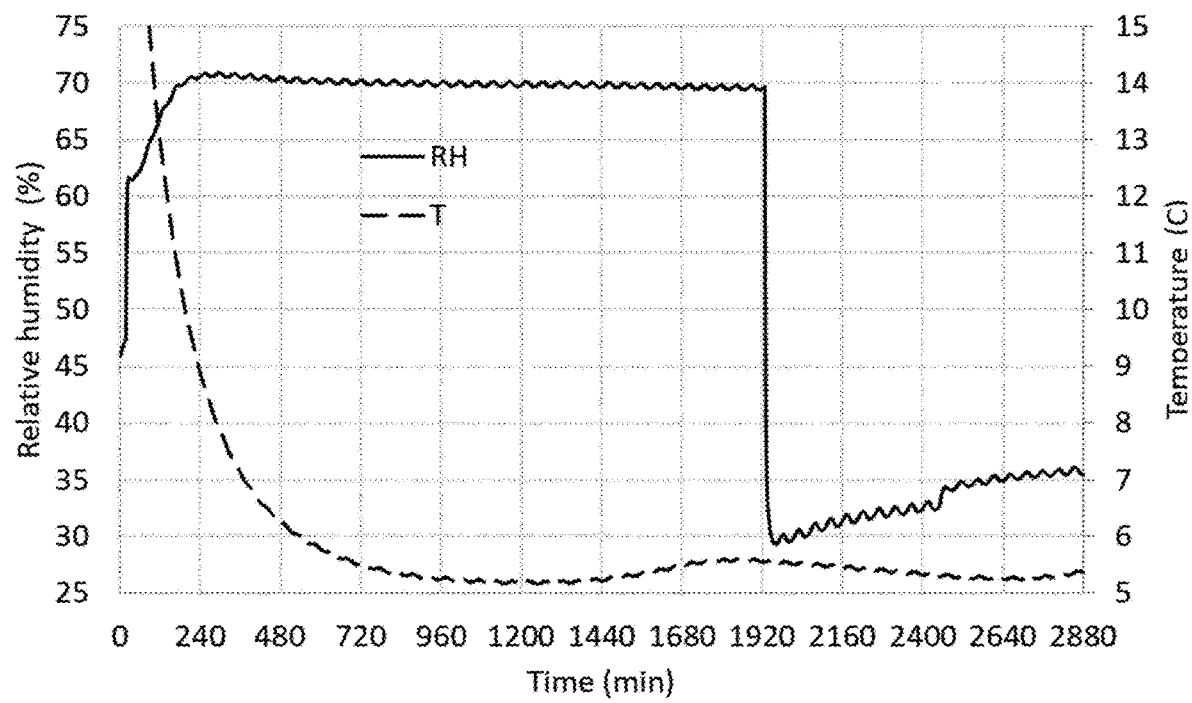
FIG. 7 is a graph of a change in humidity of dry air exposed to a humidifier and then to a NaCl or $CaCl_2$ dehumidifier at an initially reducing temperature.

FIG. 7 illustrates the humidity of air produced by exemplary apparatus in which dry air has been passed over a humidifier of a 100 ml vial containing water followed by a NaCl dry salt dehumidifier in which the apparatus at room temperature is placed in a refrigerator at time 0. The relative humidity is much more stable than that illustrated in FIG. 5; a change in humidity caused by the falling temperature is reduced by the action of the dehumidifier placed after the humidifier in the gas flow path. At 1920 minutes, the NaCl dry salt dehumidifier was replaced with flakes of $CaCl_2$) dry salt dehumidifier, causing the relative humidity to sharply decrease. It can therefore be seen that the dehumidifier may be selected according to the desired humidity.

Figure 8:
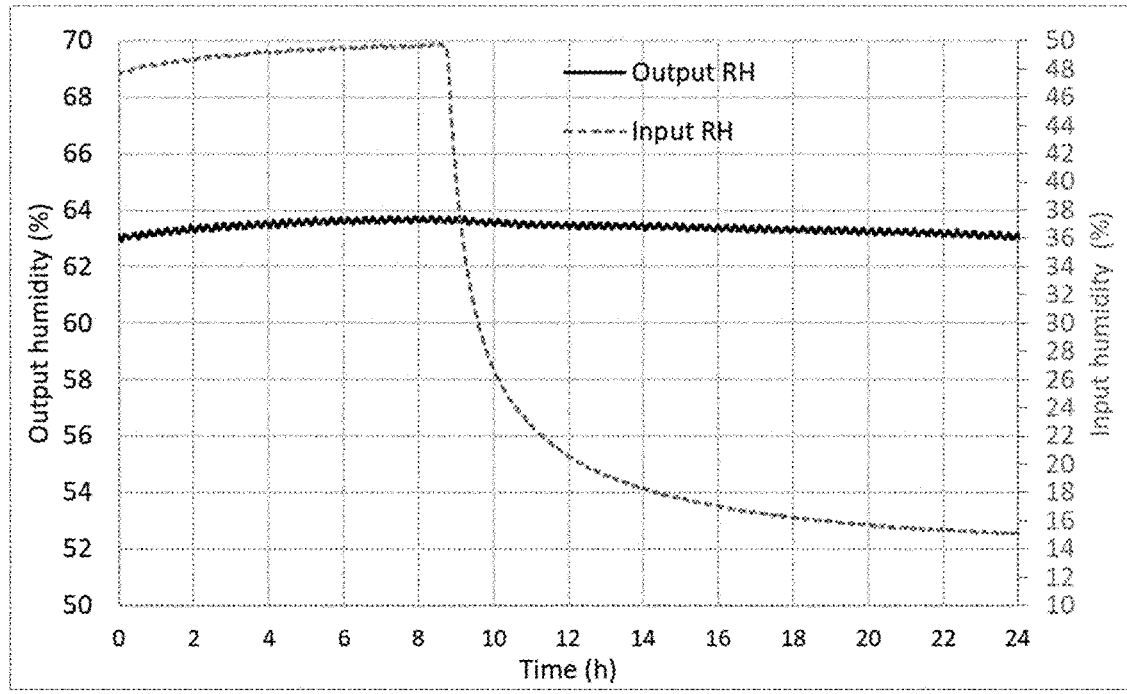
FIG. 8 is a graph of output humidity of an input gas treated with a humidifier followed by a NaCl dehumidifier across a range of input gas humidities.

FIG. 8 shows humidity of input and output gases for exemplary apparatus containing humidifier containing a gel of 5% Xanthan gum and a saturated solution of calcium formate inside a 100 ml vial followed by a dehumidifier of 20 1 g NaCl tablets inside a 40 ml vial. The input relative humidity was varied across a wide range of about 70% to 52% however the output humidity remained constant at about 63%.

Figure 9:
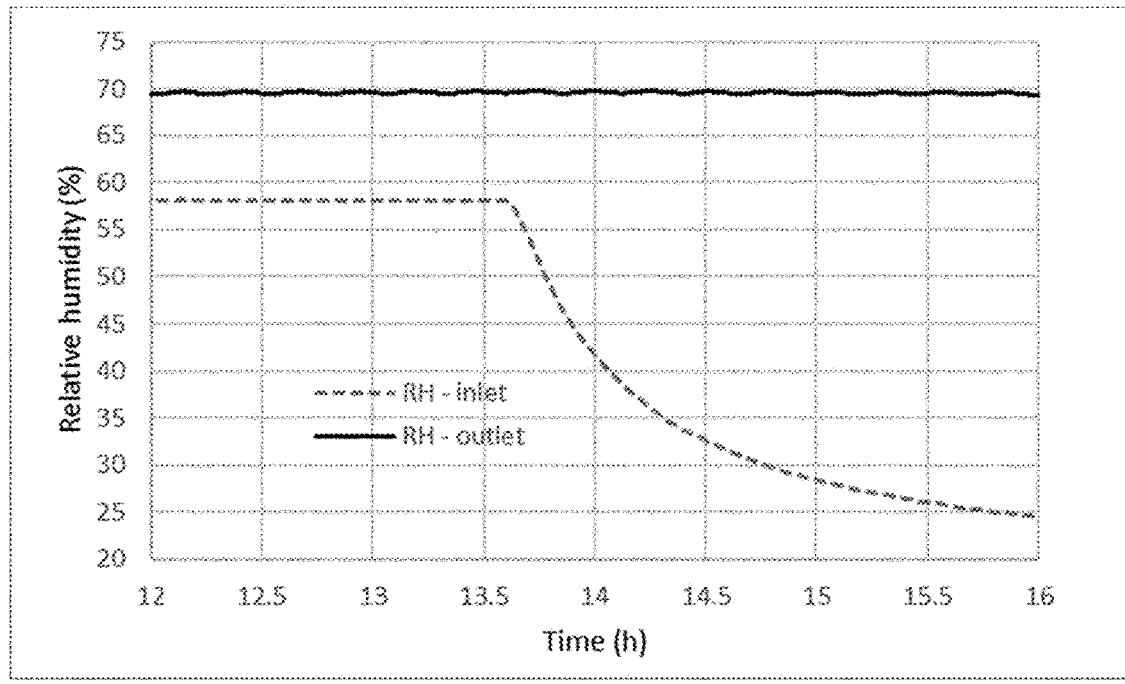
FIG. 9 is a graph of output humidity of an input gas treated with a humidifier followed by a ammonium sulfate dehumidifier across a range of input gas humidities.

FIG. 9 shows humidity of input and output gases for apparatus as described for FIG. 7 except that NaCl tablets were replaced with ammonium sulfate pellets. The output humidity remained constant at about 69% across a range of input humidities from 58% to below 30%.

Figure 10:
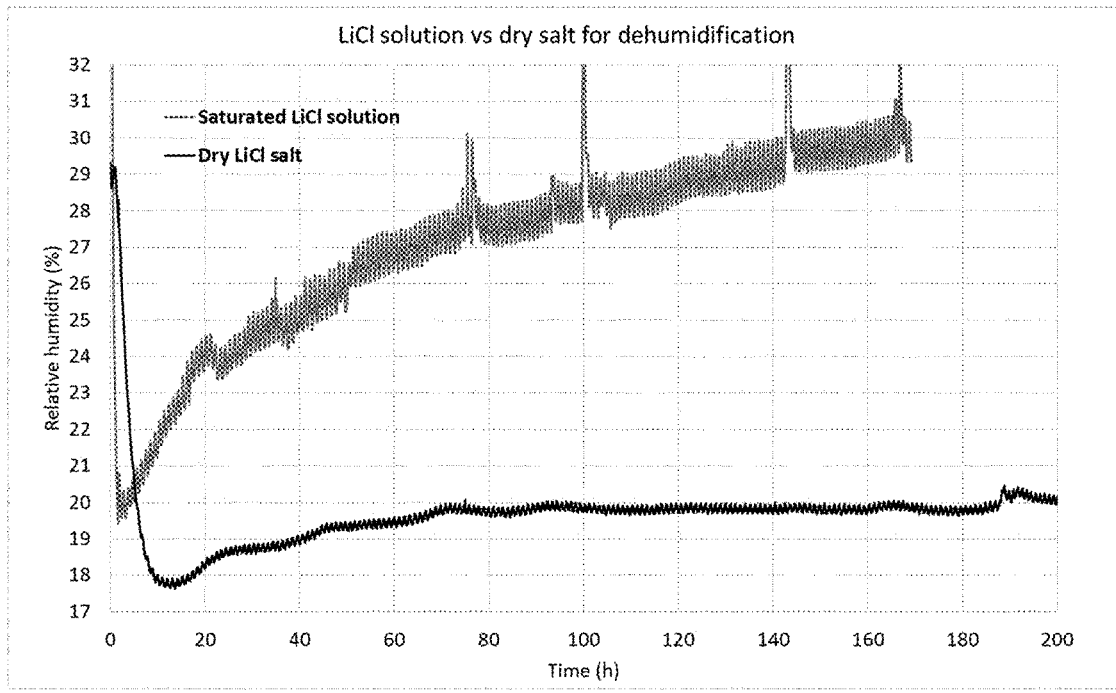
FIG. 10 shows change in humidity over time of a gas flowing over a LiCl salt solution dehumidifier and over a LiCl salt dehumidifier.

FIG. 10 shows output humidity of 90% humidity input air, formed after passing over a water-based humidifier following exposure at a 50 $cm^3$/min flow rate to a 40 ml vial containing saturated solution of LiCl and to dry LiCl salt. The humidity of the dehumidified gas is more stable over time for the gas treated with dry salt.

1-MCP concentration was measured over a 24 hour period using gas sensor apparatus illustrated in FIG. 5 with gas flowing through flow path 2.

One concentration reading was taken per hour, following a calibration and a baseline correction cycle of flowing through molecular sieve 5A filter 60 through flow path B for 45 minutes followed by 15 minutes unfiltered exposure of flow path A.

The gas sensor apparatus was located inside a cool storage room containing apples. The humidifier was calcium formate solution in a Xanthan gum gel in a 100 ml vial. The dehumidifier was ammonium sulphate pellets in a 40 ml vial.

The gas sensor 40 was a top-gate organic thin film transistor. Source and drain contacts were deposited onto a PEN substrate by thermal evaporation of 3 nm Cr followed by 40 nm Au through shadow masks with channel length of 125 μm and a channel width of 4 mm. Semiconducting Polymer 1, illustrated below, was deposited over the substrate by spin coating from a 1% w/v solution in 1,2,4-trimethylbenzene to a thickness of 40 nm and dried at 100° C. for 1 minute in air. The polymer dielectric Teflon® AF2400 was spin coated from a 2.5% w/v solution in a 50:50 v/v blend of fluorinated solvents FC43 and FC85 to a 300 nm thickness and dried at 80° C. for 10 min, after a 5 minute initial drying phase while spinning. The gate was formed by thermal evaporation of Cr (3 nm) followed by Al (200 nm) through a shadow mask to form a gate electrode having a comb structure with comb fingers of 125 microns width and gaps of 125 microns between fingers.

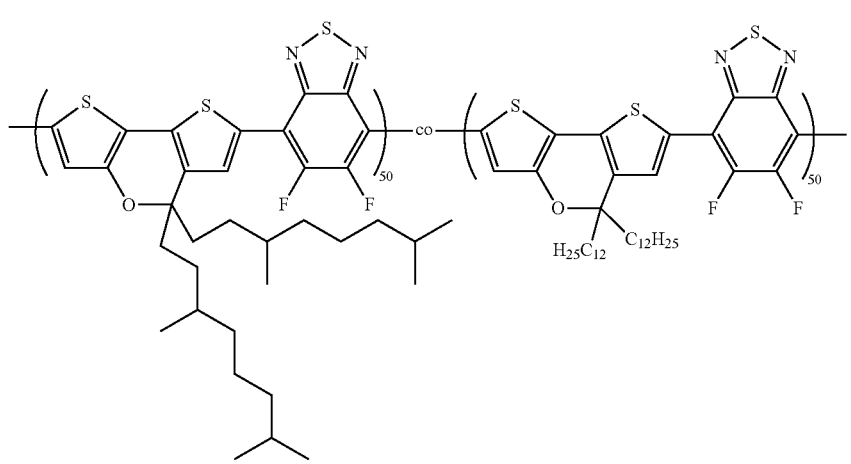

Semiconducting Polymer 1

Figure 11:
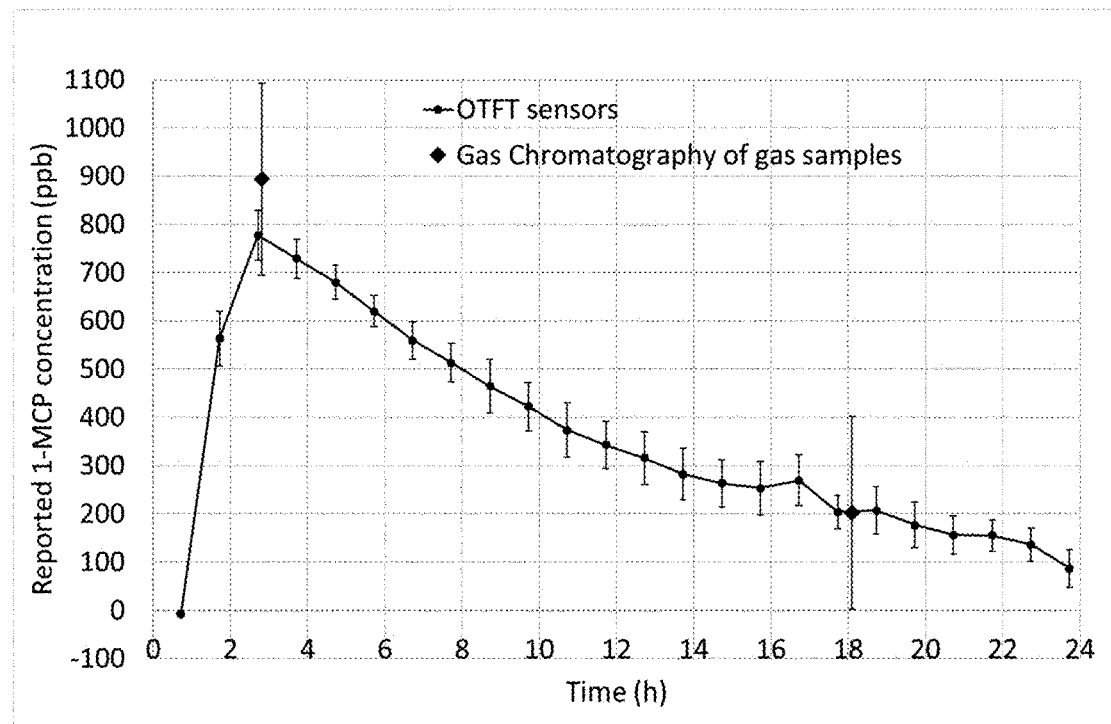
FIG. 11 is a graph of 1-MCP concentration measured using apparatus of FIG. 5.

With reference to FIG. 11, 1-MCP concentration measured by the apparatus is in agreement with measurements made by gas chromatography.

The invention claimed is:

1. A gas sensor apparatus comprising a gas inlet configured to draw gas from an environment into the gas sensor apparatus; a first gas sensor; a first gas flow path between the inlet and the gas sensor; a humidifier disposed between the gas inlet and the gas sensor in the first gas flow path of the gas sensor apparatus, wherein the humidifier is configured to form a humidifier-treated gas having a predetermined humidity level by humidification of the gas drawn from the external environment; and a dehumidifier disposed between the humidifier and the first gas sensor in the first gas flow path, wherein the dehumidifier is configured to dehumidify the humidifier-treated gas having the predetermined humidity level and wherein the first gas sensor is configured to detect the presence or concentration of a target gas in the environment, the target gas being an organic compound.

2. The gas sensor apparatus according to claim 1 wherein the dehumidifier is a solid dehumidifier.

3. The gas sensor apparatus according to claim 1 wherein the dehumidifier is a solid salt dehumidifier.

4. The gas sensor apparatus according to claim 1 wherein the humidifier is a salt solution or gel.

5. The gas sensor apparatus according to claim 1 wherein the apparatus comprises a second gas flow path between the inlet and the gas sensor.

6. The gas sensor apparatus according to claim 5 wherein the second gas flow path comprises a target gas filter disposed between the inlet and the first gas sensor wherein the target gas filter is configured to filter the target gas from an input gas.

7. The gas sensor apparatus according to claim 1 wherein the gas sensor apparatus further comprises a non-target gas filter configured to filter a gas other than the target gas.

8. The gas sensor apparatus according to claim 1 wherein the first gas flow path does not comprise a filter disposed between the inlet and the gas sensor.

9. The gas sensor apparatus according to claim 1 wherein the first gas sensor is a photoresponsive sensor, an electrochemical sensor, a resistive sensor or a capacitive sensor.

10. The gas sensor apparatus according to claim 1 wherein the gas sensor apparatus further comprises a second gas sensor.

11. The gas sensor apparatus according to claim 10 wherein the first and second gas sensors are the same.

12. The gas sensor apparatus according to claim 10 wherein the first and second gas sensors are different.

13. A method of detecting the presence or concentration of a target gas in a sample environmental gas, the method comprising:
    forming a humidifier-treated environmental gas having a predetermined humidity level comprising exposing the sample environmental gas to a humidifier;
    forming a dehumidifier-treated gas comprising exposing the humidifier-treated environmental gas having the predetermined humidity level to a dehumidifier; and
    measuring a response of a gas sensor to the dehumidifier-treated environmental gas, wherein the target gas is an organic compound.

14. The method according to claim 13 wherein the target gas is an alkene.

15. The method according to claim 14 wherein the target gas is ethylene or 1-methylcyclopropene.

* * * * *